United States Patent [19]

Belmares-Sarabia

[11] 4,038,300

[45] July 26, 1977

[54] POLYMERIZABLE ETHYLENICALLY UNSATURATED N-SUBSTITUTED 2,2-DIHYDRO CARBYL-2,1,3-BENZOSTANNA-THIAZO-LINES

[76] Inventor: Hector Belmares-Sarabia, Cuernavaca, 745 Colonial La Pastora, Villa de Guadalupe, M. L., Mexico

[21] Appl. No.: 499,879

[22] Filed: Aug. 23, 1974 (Under 37 CFR 1.47)

[51] Int. Cl.$^2$ .................................................. C07F 7/22
[52] U.S. Cl. .......................... 260/429.7; 260/45.75 S; 260/45.85 N; 260/79.3 R; 260/79.3 M; 260/79.3 MU
[58] Field of Search .................... 260/429.7, 45.75 J

[56] References Cited

U.S. PATENT DOCUMENTS 3,856,840   12/1974   O'Brien et al. .................... 260/429.7

Primary Examiner—Helen M. S. Sneed
Attorney, Agent, or Firm—Michael B. Fein; Lester E. Johnson

[57] ABSTRACT

Polymerizable ethylenically unsaturated N-substituted 2,2-dihydrocarbyl-2, 1,3-benzostannathiazolines prepared by the reaction at the amino group of a N-(aminobenzenesulfonyl)-2,2-dihydrocarbyl-2,1,3-benzostannathiazoline precursor with an ethylenically unsaturated reactant capable of alkylating or acylating said amino group. The benzostannathiazolines can be addition homopolymerized and polymerized with other monomers by means of free radical initiators to give high molecular weight polymers useful in the form of shaped objects and self-supported films, and/or as stabilizers for vinyl chloride polymers and the like.

9 Claims, No Drawings

POLYMERIZABLE ETHYLENICALLY UNSATURATED N-SUBSTITUTED 2,2-DIHYDRO CARBYL-2,1,3-BENZOSTANNA-THIAZOLINES

This invention relates to ethylenically unsaturated compounds of the formula

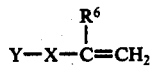
(I)

wherein Y is

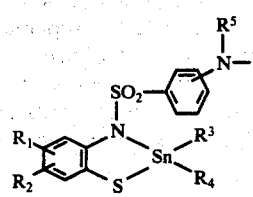
(II)

$R^1$ and $R^2$ are separately selected from the group consisting of hydrogen, halogen, lower carboalkoxy, lower alkoxy and lower hydrocarbyl; $R^3$ and $R^4$ are separately selected monovalent hydrocarbyl groups; $R^5$ is a monovalent group selected from the group consisting of hydrogen and hydrocarbyl; X is a bridging group selected from the group consisting of

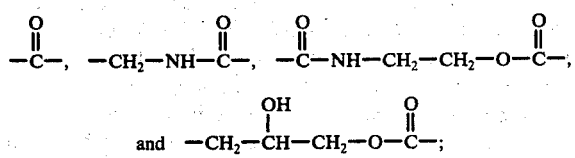

and $R^6$ is a monovalent group selected from the group consisting of hydrogen and methyl. The term "lower" as applied to an alkoxy of hydrocarbyl group refers to a group containing 1-4 carbon atoms unless otherwise indicated.

This invention is also directed to homopolymers of the ethylenic unsaturated compound (I) having the recurring unit:

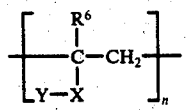
(III)

wherein $x$ is 

and $n$ is 50 to 10,000.

This invention is further directed to an interpolymer of ethylenic unsaturated compound I of this invention with at least one other ethylenic polymerizable monomer.

The polymers of this invention are used to produce molded objects and self-supporting films and as stabilizers for polyvinyl chloride polymers.

The compounds of this invention, which are acrylates, methacrylates, acrylamides and methacrylamides, can be polymerized with one or more copolymerizable monomers having the general formula

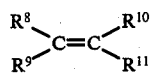
(IV)

wherein $R^8$ is chlorine, bromine, phenyl, chlorophenyl, cyano,

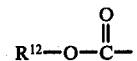

wherein $R^{12}$ is an alkyl group containing 1 to 4 carbons such as methyl, ethyl, propyl, n-butyl and the like,

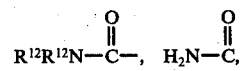

$CH_2=CH-$, or $CH_2=CCl-$, and $R^9$, $R^{10}$ and $R^{11}$ are separately selected from the group of hydrogen, alkyl and $R^8$. The characteristics of the polymers provided herein are dependent upon the monomer or monomers used in the polymerization and the molecular weight of the polymers produced. Depending upon these variables, these polymers can be hard or elastomeric solids or oils or greases.

The polymerization can be effected by heating a mixture containing a benzostannathiazoline having an ethylenically unsaturated substituent of this invention with one or more of the copolymerizable monomers described above to temperatures of the order of 100+ to 250° C. under pressures of atmospheric pressure up to 3,000 atmospheres. A mixture of a compound of this invention and one or more of the above-described monomers can also be copolymerized upon exposure to a free radical-generating source. Under such conditions, polymerization takes place even at subnormal temperatures, e.g. 0° C., although temperatures in the range of 10° to 100° C. or higher are preferred.

One source of free radicals is found in the well-known free radical-producing polymerization initiators, including, for example, diacyl peroxides such as acetyl peroxide and dibenzoyl peroxide, dialkyl peroxides such as di-tert-butyl peroxide, per salts such as ammonium and alkali metal persulfates, perborates and percarbonates, azonitriles such as 2,2'-azobisisobutyronitrile and 2,2'-bis(-2-α-dimethylvaleronitrile) and others, described in U.S. Pat. No. 2,471,959; isopropylpercarbonate, dinitrogen difluoride and other addition polymerization catalyst. Such initiators or catalysts are used in catalytic amounts with the monomer or mixture of monomers, e.g., between 0.001 and 0.05 mole per mole of total polymerizable mixture.

Another method of producing free radicals for initiation of the polymerization consists of exposiing the mixture of monomeric compounds to ultraviolet light, i.e., light of wave length in the range of about 1800 to 3800 A. units. If desired, this can be done in the presence of one of the known photopolymerization initiators such as biacetyl, benzoin, alkyl ethers of benzoin and the like. Still another free radical-generating source which can be used is the various types of ionization radiation, wherein said radiation, has an energy of the order of about 50 electron-volts or higher.

Examples of the polymerizable co-monomers used to form the copolymers include, methyl methacrylate, propyl methacrylate, butyl methacrylate, methyl acrylate, ethyl methacrylate, ethyl acrylate, propyl acrylate, butyl acrylate, methacrylamide, acrylamide, N,N-dimethylmethacrylamide, N,N-dimethylacrylamide, N-phenylmethacrylamide, N-methylacrylamide, N-butylmethacrylamide, N-butylacrylamide, vinyl acetate, vinyl chloride, vinyl fluoride, vinylidene fluoride, styrene, chlorostyrene, butadiene, chloroprene, acrylonitrile and the like.

Polymerization takes place through the ethylenically unsaturated group of the compounds of this invention and the monomers. The copolymer produced can be a block polymer, e.g., a polymer having in any one polymer molecule sections containing the same repeating unit, a random polymer, e.g., a polymer where the co-monomer units are randomly distributed in the polymer molecule, or an alternating polymer, e.g., a polymer wherein the monomer units are alternately situated in the polymer molecule.

Suitable solvents and/or dispersion media for the free-radical polymerization include water, hydrocarbons such as hexane and benzene, chlorinated aromatic hydrocarbons such as chlorobenzene, nitriles such as acetonitrile, amides such as N,N-dimethylformamide, N,N-dimethylacetamide and N-methylpyrrolidone, sulfoxides such as tetramethylenesulfoxide and the like.

The polymers preferably have a molecular weight in the range of 10,000 to 1,000,000. These polymers have an intrinsic viscosity ($\eta$) of 0.05 to 1.0 or higher dl./g. as measured in ethylene dichloride at 30° C. The estimated intrinsic viscosity (Est.[$\eta$]) can be obtained as described F. W. Billmeyer's, Textbook of Polymer Science, Interscience Publishers, N. Y. 1962.

The novel organotin heterocyclic compounds of the present invention, either as the monomer or as polymers, are particularly useful as a constituent of halogen-containing resins and compositions containing these resins. For example, a copolymer of vinyl chloride with a minor amount of compound I, for example, about ½ to 5% based on the weight of the polymer, shows improved stability against the degradative effect of light, heat and/or oxygen. In such copolymers, the polymerized compound I is a nonextractable internal stabilizer.

The organotin polymers have been found to possess low toxicity and, therefore, are useful for stabilizing polyvinyl chloride which may come into contact with foodstuffs. These copolymers are also useful as nonvolatile stabilizers for vinyl chloride polymers and copolymers. In this application the copolymer is mixed with a polyvinyl chloride and a plasticizer, for example, on a rubber mill heated to 300° F. The amount of copolymer will depend upon the mole per cent of the tin-containing moiety in the copolymer. Preferably, the total tin content of the resulting plasticized polyvinyl chloride is 0.5 to 5%, by weight.

The organotin heterocyclic compounds of this invention can be prepared by the alkylation or acylation (with an alkylating or acylating agent having ethylenic unsaturation of the product formed by reacting a compound having the structure

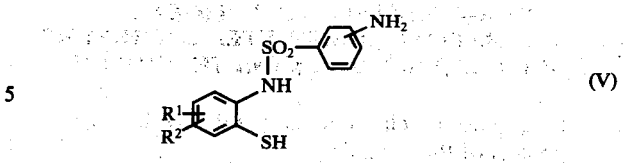

with an organotin compound having the formula

wherein $R^1$, $R^2$, $R^3$ and $R^4$ have the same significance as given hereinbefore, and Q and Z are separately, selected from the group consisting of halogen, alkoxide, and carboxylate or when taken together represent an oxygen or sulfur atom. In addition to compounds of Formula VI, related compounds having the structure

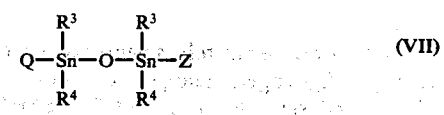

or polymeric derivatives thereof can be used.

The starting compounds of Formula V can be prepared by reduction of the corresponding disulfides according to methods described in the literature, for example, J. prakt. Chem. (4) 14, 139 (1961) and Chem. Pharmaceutical Bulletin (Tokyo) 13 (1), 33 (1965). The latter reference employed sodium sulfide for this reduction and reported that difficulties were encountered in isolating the product thiols due to their facile oxidation by air to the original disulfides. However, other techniques, such as treatment with zinc and acetic acid or tin and hydrochloric acid, electrolysis in the presence of stannous chloride, etc., may be used for reduction of the disulfide precursors. In particular, reduction with zinc and acetic acid gives good yields of the product thiols which are readily isolated and characterized.

The organotin reagents of Formula VI and/or VII are either avialable commercially or may be prepared by known procedures. Typical of the reagents which may be used as dimethyltin oxide, dibutyltin oxide, diisopropyltin oxide, di-n-octyltin oxide, di-2-ethylhexyltin oxide, n-octylbutyltin oxide, dibutyltin dichloride, di-n-octyltin dichloride, dibutyltin dimethoxide, dibutyl chlorostannoxane, etc. The reaction between compounds of Formula V and Formula VI (or VII) may be carried out in a number of alternative ways. With dialkyltin oxides, condensation is readily effected by refluxing in a hydrocarbon solvent such as benzene, toluene, etc., with removal of the water by azeotropic distillation. When dialkyltin dichlorides are used, the reaction is generally carried out at room temperature or below, in the presence of a base such as sodium methoxide, triethylamine, etc. The organotin heterocyclic compounds of this invention are monomeric in nature; that is, the molecular weight of the compound corresponds to that of Formula I as shown above. It is well known in the art that tin-nitrogen bonds are extremely sensitive to chemical attack, for example, hydrolysis. The compounds of this invention, however, are characterized by a surprising degree of stability toward cleavage of the tin-nitrogen or the tin-sulfur bonds.

The alkylation or acylation reaction can be conducted with an ethylenically unsaturated compound, for example, acryloyl chloride, methacryloyl chloride, methylol-methacrylamide, methylolacrylamide, methylol-N-methyl-methacrylamide, methylol-N-methylacrylamide, glycidyl methacrylate, glycidyl acrylate and the like.

The hydrocarbyl substituent described herein is a monovalent group of up to 18 carbons produced by the removal of a hydrogen atom from a hydrocarbon molecule. The hydrocarbyl group is free of ethylenic unsaturation. Preferably, the hydrocarbyl substituents contain up to 12 carbons and most preferred they contain up to 8 carbons. For example, hydrocarbyl can be methyl, ethyl, propyl, n-butyl, iso-butyl, n-pentyl, n-hexyl, octyl, decyl, dodecyl, hexadecyl, octadecyl, cyclohexyl, cyclopentyl, cyclohexylmethyl, phenyl, β-naphthyl, naphthyl, tolyl, xylyl, benzyl, and the like.

To assist those skilled in the art to practice the present invention, the following modes of operation are provided by way of illustration; parts and percentages are by weight and temperatures are in degrees Centrigrade unless otherwise indicated.

The reaction scheme for the production of the present invention can be initiated with known compounds such as di[o-(p-acetamidobenzenesulfonyl)aminophenyl]disulfide.

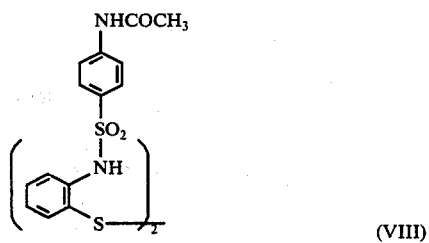

(VIII)

This compound may be synthesized according to the method of S. Mizukomi, M. Kono, Chem. Pharm. Bull. (Yokyo) 13 (1), 33 (1965).

The corresponding thiol was prepared by introducing 438 g. (0.683 mole) of compound VIII and 1.4 liters of glacial acetic acid into a 3-liter, three-necked, round-bottomed flask provided with a condenser, topped by a drying tube, and overhead stirrer and mechanical stirrer. The mixture was warmed just below its reflux temperature; 108.6 g. (1.66 moles) of zinc powder were then added in a 45-minute period. The reaction mixture became transparent and the thiol precipitate formed. It was refluxed for 18 hours with vigorous stirring, cooled to room temperature and poured into cold (0° C.) 6N hydrochloric acid with constant stirring. The powder was filtered and washed thoroughly with water and dried in a vacuum oven at 60° for 2 hours and then overnight at room temperature.

This thiol is converted to the corresponding compound of the Formula V type by introducing 183 g. (0.57 mole) of the thiol into a 5-liter, three-necked, round-bottomed flask provided with mechanical stirring, nitrogen blanket, and reflux condenser containing 2400 ml. of 10% solution of sodium hydroxide through which nitrogen had been bubbled for about 1 hour. Without interrupting the nitrogen or stirring, the reaction mixture was heated on the steam bath for three hours. It was cooled at 0° C. and added under stirring to 3.6 liters of 3N HCL cooled at 0° C. The addition was done as fast as possible to obtain a white powder without the formation of a resinous product. The pH was adjusted to 5, the powder filtered, washed with water and dried overnight at 50° C. under a vacuum. The compound was identified as:

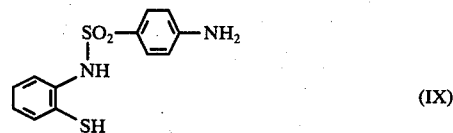

(IX)

In a 3-liter, three-necked, round-bottomed flask fitted with an overhead stirrer and a Dean-Stark trap topped by a condenser with a drying tube were placed 94.5 g. (0.34 mole) of the compound (IX) 84 g. (0.34 mole) of dibutyltin oxide and 2 liters of benzene. The reaction mixture was heated to reflux and a clear solution resulted. The water formed was azeotroped out of the reaction flask. After the theoretical amount of water (6.15 ml.) had been collected, the solution was filtered while hot and allowed to cool down. The crystals formed were filtered and dried overnight at 40° C. in a vacuum. The crystals were identified as:

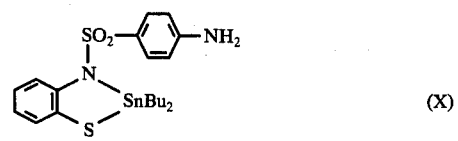

(X)

which has the structure typical of compounds useful for producing the products of the present invention.

EXAMPLE 1

In a 500-ml., three-necked round-bottomed flask provided with a condenser topped by a calcium chloride drying tube, mechanical stirrer and an addition funnel with pressure equalizer were placed 40 g. (0.08 mole) of compound X, 33.92 g. (0.32 mole) of anhydrous finely powdered sodium carbonate and 300 ml. of dried acetonitrile (dried over $P_2O_5$ and distilled). The reaction mixture, under stirring, was cooled to 0° and then keeping the temperature constant, 8.32 g. (0.08 mole) of methyacrylyl chloride was added dropwise in 4 hours. The reaction mixture was stirred for one hour more and then filtered. The filtrate was evaporated to dryness at 40°-45° C. under a vacuum. The dried material weighed 45.2 g. It was crystallized from benzene to give 44 g. (95%) of white crystals, m.p. transition at 118°-120° C. and by rubbing capillary tube it solidifies and then melts at 171°-173° C. Infrared spectrum confirms the structure as

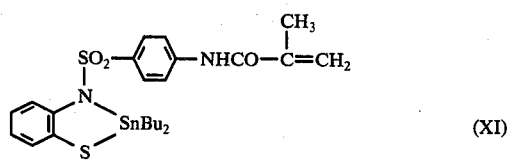

(XI)

Analysis—Calc'd. for $C_{24}H_{32}N_2O_3SSn$: C, 49.77%; H, 5.52%; N, 4.83%; S, 11.07%; Sn, 20.49. Found: C, 49.44%; H, 5.58%; N, 4.68%; S, 11.14%; Sn, 20.27%.

EXAMPLE 2

In a 100-ml., three-necked, round-bottomed flask provided with a mechanical stirrer, an addition funnel and a Frederick condenser topped with a CaCl₂ drying tube were placed 4 g. (0.008 mole) of compound X, 40 ml. of P₂O₅-dry acetonitrile, 0.100 g. of p-toluenesulfonic acid (monohydrate), and 10 mg. of the methyl ether of hydroquinone (polymerization inhibitor). The mixture was heated to reflux and 0.92 g. (0.008 mole) of methylolmethacrylamide dissolved in 10 ml. of dry acetonitrile was added in 15 minutes. The mixture was refluxed for 2 hours. The solvent was evaporated under a vacuum, the solid was dissolved in 50 ml. of boiling chloroform and 50 ml. of boiling hexane was added. The solid formed was filtered and discarded. Hexane (150 ml.) was added to the clear filtrate. The solid that formed was filtered and dried at 45° C. under vacuum overnight; m.p. 121°–123° C.

Analyis—Calc'd. for $C_{26}H_{35}N_3O_3SSn$: C, 49,35%; H, 5.79%; N, 6.90; S, 10.54; Sn, 19.50%. Found: C, 49.12%; H, 5.97%; N, 6.65%, 6.5 %; S, 10.60%, 10.61%; Sn, 19.61%; 20.08%.

The analysis corresponds to

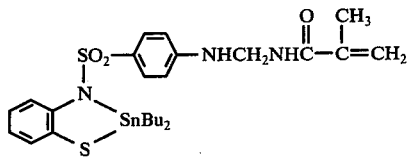

(XII)

EXAMPLE 3

In a 100-ml., three-necked, round-bottomed flask provided with a mechanical stirrer, a Frederick condenser topped with a CaCl₂ tube were placed 8.0 g. (0.0157 mole) of compound X, 50 ml. of P₂O₅-dry acetonitrile, 0.2 g. of p-toluenesulfonic acid (monohydrate), 2.23 g. (0.0157 mole) of glycidyl methacrylate, and 2 mg. of the methyl ether of hydroquinone. The reaction mixture was refluxed for 2 hours and the solvent was evaporated under vacuum. The residue was dissolved in 140 ml. of benzene and cooled down. The oily precipitate obtained in this operation was treated with 30 ml. of benzene, the benzene solutions were mixed and the insoluble precipitate was discarded. The solvent was evaporated under vacuum and the oily residue was dried at 70° C., overnight in a vacuum. The yield was 5.15 g. of a light-brown oil that solidified on standing; m.p. 56°–58° C.

Analysis—Calc'd. for $C_{26}H_{38}N_2O_5SSn$: C, 49.63%; H, 5.86%, N, 4.28%; S, 9.81%; Sn, 18.16%. Found: C, 49.63%; H, 5.95%; N, 4.33%, 4.42%, 4.41%; S, 9.83%; Sn, 18.51%, 18.66%.

The analysis corresponds to

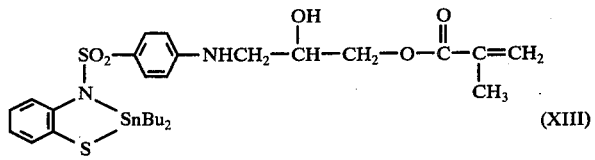

(XIII)

EXAMPLE 4

In a 100-ml., three-necked, round-bottomed flask equipped with a mechanical stirrer and a reflux condenser topped with a CaCl₂ tube were placed 4.0 g. (0.008 mole) of compound X, 65 ml. of P₂O₅-dry benzene, 10 ml. of O=C=N—CH₂≃CH₂OOCC(CH₃)CH₂ (ICEMA), 1.136 ml. of dibutyltin dilaurate (catalyst). The reaction mixture was refluxed for 3½ hours, cooled to room temperature and added to 800 ml. of hexane. The precipitate was recrystallized from 40 ml. of dry benzene. The crystals were dried overnight at 50° C. in a vacuum oven; m.p. 110°–112° C.

Analysis—Calc'd. for $C_{27}H_{37}N_3O_5SSn$: C, 48.66%; H, 5.59%; N, 6.30%; S, 9.62%; Sn, 17.80%. Found: C, 48.80%; H, 5.60%, N, 6.30%; S, 9.68%; Sn, 17.65%.

This analysis corresponds to

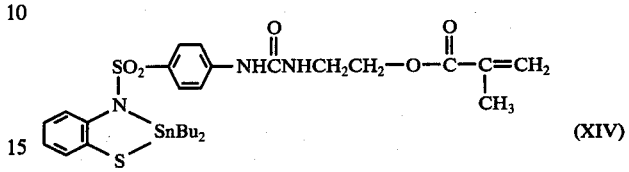

(XIV)

EXAMPLE 5

The procedure of Example 1 is repeated except that an equivalent mole amount of acryloyl chloride is used instead of methacrylyl chloride. Infrared data of the product indicate that the structure is

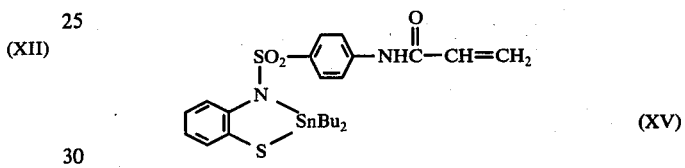

(XV)

A melting point transition was observed at 105°–107° C.; m.p. 159°–160° C.

Analysis—Calc'd. for $C_{23}H_{30}N_2O_3SSn$: N, 4.95%; S, 11.34%; Sn, 20.99%. Found: N, 5.15%, 5.08%; S, 11.09%, 11.18%; Sn, 19.56%, 19.49%.

EXAMPLE 6

The procedure of Example 1 was repeated except that an equivalent molar amount of N-(aminobenzenesulfonyl-2,2-di-n-octyl-2,1,3-benzostannathiazoline was used. The product had a melting point transition of 129°–130° C. and melted at 136°–137° C.

Analysis—Calc'd. for $C_{32}H_{48}N_2O_3SSn$: C, 55.57%; H, 6.99%; N, 4.05%; S, 9.27%; Sn,
Found: C, 55.89%, 56.12%; H, 6.87%, 7.00%, 6.87%; N, 4.07%, 3.85%, 4.11%; S, 9.21%; Sn, 16.43%, 16.20%.

The analysis corresponds to

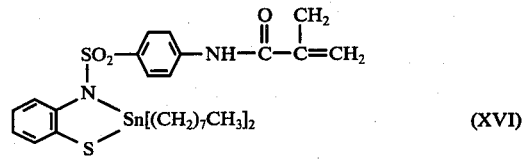

(XVI)

The procedures outlined in Examples 1–6 can be used to produce the compounds of this invention substituting the following benzostannathiazolines instead of the benzostannathiazolines shown:

N-(aminobenzenesulfonyl)-2,2-dilauryl-2,1,3-benzostannathiazoline

N-(aminobenzenesulfonyl)-2,2-di-2-ethylhexyl-2,1,3-benzostannathiazoline

N-(aminobenzenesulfonyl)-2-butyl-2-octyl-2,1,3-benzostannathiazoline

N-(aminobenzenesulfonyl)-2-butyl-2-isohexyl-2,1,3-benzostannathiazoline

N-(aminobenzenesulfonyl)-2-butyl-2-phenyl-2,1,3-benzostannathiazoline

N-(aminobenzenesulfonyl)-2,2-dicyclohexyl-2,1,3-benzostannathiazoline

N-(aminobenzenesulfonyl)-2,2-diphenyl-2,1,3-benzostannathiazoline

N-(aminobenzenesulfonyl)-2,2-dibenzyl-2,1,3-benzostannathiazoline

N-(aminobenzenesulfonyl)-2,2-diisopropyl-2,1,3-benzostannathiazoline

N-(aminobenzenesulfonyl)-2,2-ditolyl-2,1,3-benzostannathiazoline

N-(aminobenzenesulfonyl)-2,2-dixylyl-2,1,3-benzostannathiazoline

N-(aminobenzenesulfonyl)-2,2-distearyl-2,1,3-benzostannathiazoline

N-(aminobenzenesulfonyl)-2,2-didecyl-2,1,3-benzostannathiazoline

N-(aminobenzenesulfonyl)-2,2-didodecyl-2,1,3-benzostannathiazoline

EXAMPLE 7

A sample of 32.5 g. of methyl methyacrylate and 17.5 g. of the product of Example 1 were mixed and heated to 60° C/; then 0.016 g. (0.03%) of 2,2'-azobisisobutyronitrile (AIBN) and 0.45 g. (0.9%) of n-dodecyl mercaptan were added. The solution was placed in a polyvinyl alcohol bag and polymerized at 66° C. for 24 hours. The hard copolymer was soluble in ethylene dichloride (EDC). The estimated intrinsic viscosity in ethylene dichloride at 30° C. was 0.59 dl/g.

EXAMPLE 8

In a 300-ml., three-necked, round-bottomed flask provided with a mechanical stirrer, nitrogen bubbler and a condenser were placed 50 g. of the product of Example 1, 150 ml. of acetonitrile, 0.081 g. of AIBN and 0.200 g. of n-dodecyl mercaptan. Nitrogen was bubbled for 1 hour and then the solution was heated at 70° C. for several hours. The viscous solution was poured in benzene and the precipitate was filtered. The estimated intrinsic viscosity in acetone was 0.26. The polymer is soluble in methanol and acetone and insoluble in EDC. The infrared spectrum is almost identical to the spectrum of the product of Example 1 except for methacrylamide double bond. Elemental analysis confirmed the structure.

EXAMPLE 9

In a 300-ml., three-necked, round-bottomed flask provided with a mechanical stirrer, nitrogen bubbler and a condenser is placed 53 g. (0.097 mole) of the product of Example 1, 18 g. (0.18 mole) of methyl methacrylate, 250 ml. of acetonitrile and 0.021 g. (1.3×10-5 mole) of AIBN and the procedure of Example 8 was followed. A high molecular weight copolymer was obtained. The acetonitrile solvent can be stripped from the polymer by vacuum distillation. The process can be repeated using 0.45 g. of n-dodecyl mercaptan as a chain transfer agent.

EXAMPLE 10

The procedure of Example 9 was repeated except that 18 g. (0.21 mole) of ethyl acrylate were added to the polymerization mixture and 0.04 g. (2.44×10-5 mole) of AIBN were used. A terpolymer soluble in n-butanol was obtained.

The process of Example 10 was followed to form the terpolymers and tetrapolymers of the product of Example 1. These polymers were dissolved in n-butanol to form the following solutions in which percentages are by weight:

EXAMPLE 11 methyl methacrylate (53%) ethyl acrylate (18%)/product of Example 1 (18%)/n-butanol (11%).

EXAMPLE 12 methyl methacrylate (53%)/butyl acrylate (18%)/product of Example 1 (18%)/n-butanol (11%).

EXAMPLE 13 methyl methacrylate (36%)/butyl acrylate (36%)/product of Example 1 (18%)/n-butanol (10%).

Example 14 methyl methacrylate (40%)/butyl acrylate (40%)/product of Example 1 (20%).

EXAMPLE 15 methyl methacrylate (40%)/ethyl acrylate (40%)/product of Example 1 (20%).

EXAMPLE 16 methyl methacrylate (36%)/ethyl acrylate (36%)/product of Example 1 (18%)/butanol (10%).

EXAMPLE 17 methyl methacrylate (53%)/ethyl acrylate (9%)/butyl acrylate (9%)/product of Example 1 (18%)/butanol (11%).

The procedures of Example 7-17 can be repeated except that a corresponding amount of one of the compounds of Examples 2-6 is used instead of the compound of Example 1.

Other polymers can be prepared using well known solution polymerization techniques. For example, polymerizable monomers such as styrene, vinyl chloride, vinyl acetate, acryloylamide, N,N-dimethylacryloylamide, butadiene, chlorobutadiene, chlorostyrene and the like. Copolymer can be prepared using the procedure of Examples 9-16 except that one or more of these comonomers is used with or instead of the acrylate or methacrylate listed.

The polymerizable ethylenically unsaturated heterocyclic compounds of this invention are useful for preparing polymers from which self-supporting films and molded objects can be prepared. Lower molecular weight polymers produced therefrom are useful as adhesive and for the coating, binding and impregnation of fibrous materials. These heterocyclic compounds are particularly useful for the preparation of vinyl chloride interpolymers having good thermal stability.

The polymers of this invention can be converted into self-supporting films and molded objects by compression molding at elevated temperature. For example, the polymers can be placed in the void of a matched-die mold heated at a temperature above the melting point of the polymer and the mold subjected to high pressures. In general, molding can be conducted at temperatures of 150° to 300° C. and pressures of 500 to 10,000 p.s.i.

Plasticized film and sheet of interpolymers of vinyl chloride and the compounds of this invention can be produced by mixing a mixture of the polymer and a plasticizer such as dioctyl phthalate, didecyl phthalate, dioctyl adipate, didecyl adipate and the like on a heated rubber mill or a three roll calender. The rolls of the rubber mill or calender should be heated to temperatures of the order of 300° to 400° F. A small amount in the order of 0.5 to 5%, by weight, of the weight of the polymer of a mixture of barium and cadium organic acid salts well-known as polyvinyl chloride stabilizers can be used.

Solutions of the methacrylate, acrylate, and acrylamide polymers with the compounds of this invention are useful for the production of a protection coating on a substrate. In this process, the solution of the polymer is coated or sparged onto a substrate such as a metal or wood and the solvent is allowed to evaporate. These solutions are also useful as adhesives.

The polymers of this invention, particularly those produced in Examples 9–16 and those produced using other comonomers are useful as nonvolatile, nonextractable, nontoxic stabilizers for polyvinyl chloride polymers and copolymers. In this application a sufficient amount of the polymer is milled into the polyvinyl chloride polymer or copolymer or into a mixture of the polyvinyl chloride and plasticizer to yield a final product containing 0.5 to 5% tin. Milling can be accomplished conveniently on a rubber mill heated to 300°–400° F. The stabilized polyvinyl chloride polymer can be converted into a sheet, self-supporting film or other objects by compression molding. Other stabilizers and additives to polyvinyl chloride such as phosphites, barium-cadmium salts, tin stabilizers and the like can be used with the polymers of this invention to stabilize vinyl chloride and other halogen-containing polymers. Halogen-containing polymers containing the polymers of this invention are resistant to the degradative effects of heat, light and oxygen on the halogen-containing polymers.

The foregoing detailed description has been given for clarity of understanding only and no unnecessary limitations are to be understood therefrom. The invention is not limited to the exact details shown and described for obvious modifications will be apparent to those skilled in the art.

The embodiments of the invention in which an exclusive property or privilege is claimed are defined as follows:

1. The ethylenically unsaturated organotin heterocyclic compounds of Formula I shown as follows:

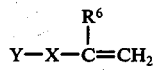

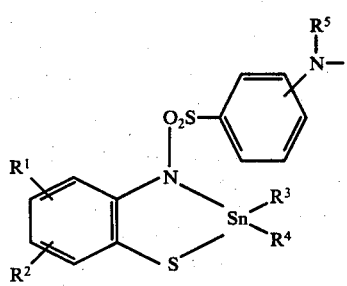

Formula I, wherein

Y is $R^1$ and $R^2$ are separately selected from the group consisting of hydrogen, halogen, lower carboalkoxy, lower alkoxy, and lower hydrocarbyl, the term "lower" referring to a group containing 1–4 carbon atoms unless otherwise indicated;

$R^3$ and $R^4$ are separately selected monovalent hydrocarbyl groups;

$R^5$ is a monovalent group selected from the group consisting of hydrogen and hydrocarbyl;

X is a bridging group selected from the group consisting of

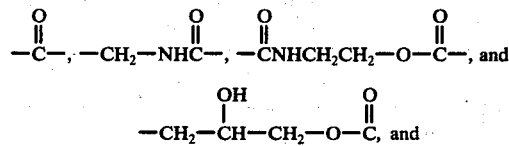

$R^6$ is a monovalent group selected from the group consisting of hydrogen and methyl.

2. The compounds of claim 1 wherein $R^1$ and $R^2$ are hydrogen.

3. The compound of claim 2 wherein $R^3$ and $R^4$ are alkyl groups containing up to 12 carbons.

4. The compound of claim 2 wherein $R^3$ and $R^4$ are aryl groups containing up to 10 carbons.

5. The compound of claim 1 wherein $R^1$ is hydrogen, $R^2$ is selected from the group consisting of methyl, octyl, phenyl, para-tolyl and naphthyl, $R^3$ and $R^4$ can be the same or different and are selected from the group consisting of methyl, n-butyl, or n-octyl, $R^5$ is a monovalent group selected from the group consisting of hydrogen and hydrocarbyl and $R^6$ is selected from the group consisting of hydrogen and methyl.

6. The compound of claim 2 having the formula

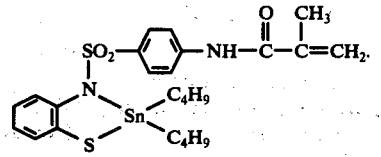

7. The compound of claim 2 having the formula

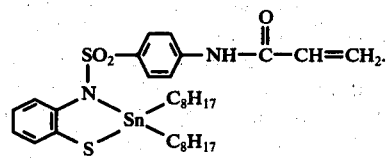

8. The compound of claim 2 having the formula

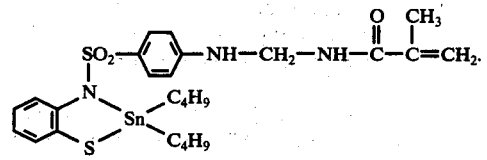

9. The compound of claim 2 having the formula

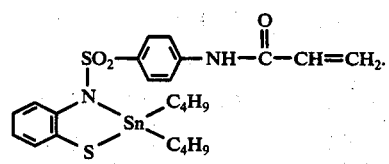

* * * * *